United States Patent [19]

Szarvas et al.

[11] Patent Number: 4,579,686

[45] Date of Patent: Apr. 1, 1986

[54] PROCESS FOR THE PREPARATION OF EASY-FLOWING (FLOWABLE) OXYTETRACYCLIN HYDROCHLORIDE

[75] Inventors: Miklós Szarvas, Debrecen; Éva Horváth née Fehér, Budapest; László Cséke; János Bálint, both of Debrecen; Ferenc Fábián; Lajos Kun, both of Debrecen, all of Hungary

[73] Assignee: Biogal Gyogyszergyar, Debrecen, Hungary

[21] Appl. No.: 606,348

[22] Filed: May 2, 1984

[30] Foreign Application Priority Data

May 2, 1983 [HU] Hungary ............................. 1495

[51] Int. Cl.$^4$ ........................................... C07C 103/26
[52] U.S. Cl. ............................... 260/351.6; 260/351.1
[58] Field of Search ........................... 260/351.6, 351.1

[56] References Cited

U.S. PATENT DOCUMENTS

| | | | |
|---|---|---|---|
| 2,516,080 | 7/1950 | Sobin et al. | 260/351.6 |
| 2,658,078 | 11/1953 | Blase | 260/351.6 |
| 2,867,661 | 1/1959 | Buckley, Jr. et al. | 260/351.6 |
| 2,929,837 | 3/1960 | Ogawa et al. | 260/351.6 |

FOREIGN PATENT DOCUMENTS

| | | |
|---|---|---|
| 143911 | 1/1958 | Hungary . |
| 160457 | 7/1973 | Hungary . |
| 49215 | 3/1965 | Poland . |
| 718032 | 11/1954 | United Kingdom . |
| 718027 | 11/1954 | United Kingdom . |
| 718020 | 11/1954 | United Kingdom . |

*Primary Examiner*—Richard L. Raymond
*Assistant Examiner*—Raymond Covington
*Attorney, Agent, or Firm*—Karl F. Ross; Herbert Dubno

[57] ABSTRACT

The invention relates to a new process for the preparation of easy-flowing (flowable) oxytetracyclin hydrochloride. According to the process of the invention, the crude, dry or filter-wet oxytetracyclin hydrochloride consisting of needle-shaped crystals is boiled with an organic solvent forming an azeotropic mixture with water, optionally a part of the solvent is distilled off in a form of an azeotropic mixture, then the mixture is cooled and the precipitated oxytetracyclin hydrochloride consisting of spherical crystals is separated and dried.

Oxytetracyclin hydrochloride exists in two various crystal forms, the one of which is needle-shaped, while the other one consists of orthorhombic sheets. The crystals of this latter form are capable of forming spherical particles by coalescence. The crystal form consisting of spherical particles is much more useful for the pharmaceutical industry.

By means of the new process easy-flowing (flowable) oxytetracyclin hydrochloride can be prepared in a favorable yield and with a high purity from the crude hydrochloride product consisting of needle-shaped crystals.

3 Claims, No Drawings

PROCESS FOR THE PREPARATION OF EASY-FLOWING (FLOWABLE) OXYTETRACYCLIN HYDROCHLORIDE

This invention relates to a simple process performable on an industrial scale for the preparation of easy-flowing (flowable) oxytetracyclin (OTC) hydrochloride.

OTC hydrochloride is a broad-spectrum antibiotic belonging to the tetracyclins and is used both in the human and veterinary medicine as well as an intermediate for the synthesis of other OTC derivatives of high purity.

OTC hydrochloride shows a polymorphism in the solid state as two crystal forms of it are known. One of these is a product consisting of long needles, while the other one is a crystalline mass of stubby, orthorhombic sheets containing no water [Ann. New York Acad. Sci. 53, 229 (1950–1951); J. Am. Chem. Soc. 73, 4211 (1951); J. Am. Chem. Soc. 74, 841 (1952)]. When the latter one crystallizes out from a solution of an appropriate concentration, then the sheets form a spherical shape by coalescence.

This latter product consisting of easy-flowing (flowable) spherical crystals is more suitable for the preparation of pharmaceutical compositions than the needle-shaped crystals, as it is not hygroscopic and does not become electrostatically charged up. Thus, it can be more easily handled and filled into the formulating equipments, furthermore its water content can rapidly be diminished by a simple drying process to below a value of 2 percent as required by the official Pharmacopoeas, whereas the product consisting of needle-shaped crystals must be dried at 50° C. under reduced pressure for a long time. An other advantage of the spherical shape appears in that it decreases the surface in relation to the volume; thus, the damaging effects of various factors, e.g. of light and moisture are diminished which results in a higher stability.

According to the hitherto known methods the needle-shaped OTC hydrochloride is prepared by treating a solution of OTC with hydrochloric acid (c.f. British patent specifications Nos. 718,020 and 718,032; U.S. Pat. No. 2,516,080) or with gaseous hydrogen chloride dissolved in an aliphatic alcohol (c.f. Belgian patent specifications Nos. 632,331 and 638,881; Hungarian patent specification No. 143,911) or with a methanolic solution of an alkaline earth metal chloride (c.f. U.S. Pat. Nos. 2,658,078 and 2,873,276; British patent specification No. 718,027; Hungarian patent specification No. 160,457).

All the above processes provide needle-shaped OTC hydrochloride crystals containing about 6 to 11 percent of water. This substance cannot exactly be weighed for the formulation as it is hygroscopic; it can be portioned only with difficulties as it has electrostatic properties; the losses are high as a consequence of the adhesion; and the stability of the product is deteriorated due to the content of water of crystallization.

According to the U.S. Pat. No. 2,867,661 a non-hygroscopic product can be prepared in such a way that the substance recrystallized from methanol is refluxed with an organic solvent, e.g. acetone, benzaldehyde, furfurol, an aliphatic alcohol containing 2 to 4 carbon atoms or lower ethers of ethyleneglycol or with a mixture of these solvents. The obtained OTC hydrochloride is less hygroscopic; however, the content of spherical crystals in that is still not sufficient.

According to the Polish patent specification No. 49,215 OTC hydrochloride prepared by fermentation can be transformed to an easy-flowing (flowable) product consisting of spherical crystals and possessing a bulk density of higher than 0.6 kg./liter by recrystallization from a mixture containing concentrated hydrochloric acid and two solvents, i.e. an aliphatic alcohol and an aliphatic ketone containing less than five carbon atoms. This recrystallized product is useful for preparing appropriate pharmaceutical formulations. A disadvantage of this method consists in the use of ternar solvent mixtures, i.e. mixtures comprising three different solvents.

The object of the invention is to provide a process for the preparation of an easy-flowing (flowable), crystalline OTC hydrochloride from a crude product, by the means of which the target product consisting of spherical crystals is obtained on an industrial scale in a high yield, with a better purity, in a more economical and simple way as compared to the processes known at present.

Surprisingly, it was found that an easy-flowing (flowable), anhydrous OTC hydrochloride consisting of spherical crystals can be obtained in such a way that the crude OTC hydrochloride consisting of needle-shaped crystals is boiled with an organic solvent forming an azeotropic mixture with the water content present, optionally a part of this azeotropic mixture is distilled off and the OTC hydrochloride consisting of spherical crystals precipitated from the cooled mixture is separated and dried.

According to the process of the invention the OTC hydrochloride consisting of needle-shaped crystals is boiled either as dry or as filter-wet with a solvent forming an azeotropic mixture with water. Suitable solvents are the esters prepared from lower aliphatic alcohols with acetic acid, e.g. ethyl acetate. The suspension of the crude product consisting of needle-shaped crystals in an alkyl acetate is stirred at 55° to 120° C. for 10 to 60 minutes, whereby the total amount of the salt is transformed to the desired crystal form and becomes practically anhydrous. The crystal water content of the OTC hydrochloride forms an azeotropic mixture with the solvent; thus, the hydrochloride is constrained to crystallize without water. The chemical contaminations which are less polar than OTC hydrochloride remain dissolved in the ethyl acetate, a phenomenon which can be recognized from the deeper color of the solution.

In general, it is sufficient to cool the mixture for initiating the crystallization. However, by using a filter-wet crude product the adherent water also forms an azeotropic mixture. It is suitable in this case to distil off a part of the water in the form of an azeotropic mixture before crystallization. The precipitated OTC hydrochloride contains 99 to 100 percent of active ingredient, while its water content is less than 1 percent.

The OTC hydrochloride consisting of spherical crystals is easy-flowing (flowable); thus, it can easily be poured and stirred. These properties are favourable and valuable for the preparation of the various formulations, e.g. capsules or powder ampoules, as the preparation of the homogenized powder mixtures becomes more easy and the losses occuring in the course of the automatic portioning are lower.

The process of the invention is further illustrated in detail by the following Examples.

EXAMPLE 1

20 g. of dry OTC hydrochloride consisting of needle-shaped crystals (with an active ingredient content of 92%) were suspended in 80 ml. of ethyl acetate. The mixture was heated in a water bath to the boiling point while stirring and refluxed for 30 minutes. During the boiling a precipitation of light yellow crystals of OTC hydrochloride occurred from the hot solution. Then, the mixture was cooled to room temperature, the crystals were filtered, washed with 25 ml. of ethyl acetate and dried by air heated to 50° C.

In this way 18.16 g. (98% yield) of OTC hydrochloride consisting of spherical crystals, containing 99.3% of active ingredient and 0.4% of water, were obtained. This product satisfies the requirements of the British Pharmacopoea 1980 (B.P. 80) as well as those of the Pharmacopoea of the United States Ed. 1980 (USP XX).

EXAMPLE 2

20 g. of dry OTC hydrochloride consisting of needle-shaped crystals (with an active ingredient content of 92%) were suspended in 80 ml. of n-butyl acetate. The mixture was heated to the boiling point and refluxed for 30 minutes. The crystallization and the separation of the crystals were carried out according to Example 1.

In this way 17.82 g. (97% yield) of OTC hydrochloride consisting of spherical crystals, containing 99.1% of active ingredient and 0.8% of water, were obtained. Other parameters of the product were in accordance with those of the product prepared according to Example 1.

EXAMPLE 3

A filter-wet filter cake containing 20 g. of crude product was suspended in 80 ml. of ethyl acetate. This suspension was heated to the boiling point and stirred at 80° C. in a water bath for 30 minutes. During this time 20 ml. of an azeotropic mixture were distilled off. The mixture was cooled to room temperature, the crystals were filtered, washed with 25 ml. of ethyl acetate and dried by air heated to 50° C.

In this way 18.8 g. (94% yield) of OTC hydrochloride consisting of spherical crystals, containing 99.8% of spherical crystals, containing 99.8% of active ingredient and 0.2% of water, were obtained.

What we claim is:

1. A process for the preparation of flowable oxytetracycline hydrochloride in the form of spherical crystals which comprises the steps of:
    (a) suspending a dried or filter-wet crude oxytetracycline hydrochloride in the form of needle-shaped crystals containing water in an organic solvent consisting of a $C_1$–$C_4$ alkyl ester of acetic acid;
    (b) boiling the suspension formed in step (a) to form both a precipitate of oxytetracycline hydrochloride in the form of spherical crystals and an azeotropic mixture of the organic solvent and water, said water being the water present initially in the crude oxytetracycline hydrochloride in the form of needle-shaped crystals;
    (c) cooling the precipitate of oxytetracycline hydrochloride in the form of spherical crystals and the azeotropic mixture of the organic solvent and water to room temperature;
    (d) separating the oxytetracyline hydrochloride in the form of spherical crystals from the azeotropic mixture; and
    (e) drying the oxytetracycline hydrochloride in the form of spherical crystals so that the water content thereof is less than 1%.

2. The process defined in claim 1 wherein following step (b) at least part of the azeotropic mixture of organic solvent and water is distilled off.

3. The process defined in claim 2 wherein the oxytetracycline hydrochloride thus obtained in the form of spherical crystals has a water content of 0.2%.

* * * * *